(12) United States Patent
Li et al.

(10) Patent No.: US 10,028,985 B2
(45) Date of Patent: Jul. 24, 2018

(54) WEIGHT LOSS FORMULATIONS, METHODS, AND COMPOSITIONS BASED ON TRADITIONAL CHINESE MEDICINE

(71) Applicants: Xiu-Min Li, Mamaronek, NY (US); Danna Chung, New York, NY (US); Nan Yang, Flushing, NY (US)

(72) Inventors: Xiu-Min Li, Mamaronek, NY (US); Danna Chung, New York, NY (US); Nan Yang, Flushing, NY (US)

( * ) Notice: Subject to any disclaimer, the term of this patent is extended or adjusted under 35 U.S.C. 154(b) by 0 days.

(21) Appl. No.: 15/101,182

(22) PCT Filed: Dec. 3, 2014

(86) PCT No.: PCT/US2014/068396
§ 371 (c)(1),
(2) Date: Jun. 2, 2016

(87) PCT Pub. No.: WO2015/084973
PCT Pub. Date: Jun. 11, 2015

(65) Prior Publication Data
US 2016/0296573 A1    Oct. 13, 2016

Related U.S. Application Data

(60) Provisional application No. 61/911,041, filed on Dec. 3, 2013.

(51) Int. Cl.
| | |
|---|---|
| *A61K 36/00* | (2006.01) |
| *A61K 36/074* | (2006.01) |
| *A61K 36/752* | (2006.01) |
| *A61K 36/481* | (2006.01) |
| *A61K 36/62* | (2006.01) |
| *A61K 36/718* | (2006.01) |
| *A61K 36/732* | (2006.01) |

(52) U.S. Cl.
CPC .......... *A61K 36/074* (2013.01); *A61K 36/481* (2013.01); *A61K 36/62* (2013.01); *A61K 36/718* (2013.01); *A61K 36/732* (2013.01); *A61K 36/752* (2013.01); *A61K 2236/00* (2013.01)

(58) Field of Classification Search
CPC .................................................... A61K 36/00
See application file for complete search history.

(56) References Cited

FOREIGN PATENT DOCUMENTS

CN    101607051 B    6/2011

OTHER PUBLICATIONS

Hoo, R. et al., "The effective fraction isolated from Radix Astragali alleviates glucose intolerance, insulin resistance and hypertriglyceridemia in db/db diabetic mice through its anti-inflammatory activity", Nutrition & Metabolism, (2010), 7:67, 12 pages.
Kim, H.L. et al., "Comi Fructus Containing Formulation Attenuates Weight Gain in Mice with Diet-Induced Obesity and Regulates Adipogenesis through AMPK", Evidence-Based Complementary and Alternative Medicine, (2013), Article ID 423741, 12 pages.
Seto, S.W. et al., "Novel hypoglycemic effects of Ganoderma lucidum water-extract in obese/diabetic (+db/+db) mice", Phytomedicine 16 (2009) 426-436.
Xiao, C. et al., "Hypoglycemic Effects of Ganoderma lucidum Polysaccharides in Type 2 Diabetic Mice", Arch Pharm Res vol. 35, No. 10, 1793-1801, 2012.
Xie, W. et al., "Effects and Action Mechanisms of Berberine and Rhizoma coptidis on Gut Microbes and Obesity in High-Fat Diet-Fed C57BL/6J Mice", PLoS ONE, (Sep. 2011), vol. 6, Issue 9, 10 pages.
You, J.S. et al., "Anti-obesity and hypolipidaemic effects of Nelumbo nucifera seed ethanol extract in human pre-adipocytes and rats fed a high-fat diet", J Sci Food Agric, (2014); 94: 568-575.
International Search Report dated Apr. 17, 2015 issued in PCT/US2014/068396.

*Primary Examiner* — Qiuwen Mi
(74) *Attorney, Agent, or Firm* — Scully, Scott, Murphy & Presser, P.C.

(57) ABSTRACT

The present invention relates to formulations made up from extracts from *Ganoderma lucidum*, rhizome of *Coptis chinensis*, *Radix astragali*, *Nelumbo nucifera* Gaertn, *Chaenomeles speciosa*, and *Fructus Aurantii*. Pursuant to the invention, the formulations are used to treat obesity and the biological sequelae of obesity including cholesterol levels and glucose levels. While not limited to any particular mechanism of action the formulations may assert their effects by altering gene expression, in particular, the expression of PPARγ, FABP4, CPT1, UCP2, and AMPK.

42 Claims, 9 Drawing Sheets

A Exp 1

B Exp 2

A

HFD/Sham  HFD/WL-1

B

HFD/Sham  HFD/WL-1

C

A

B

Table 1. Safety and biochemical analysis of WL-1

|  | Treatment | Dose | Time | Death (12hrs) | Death (24hrs) | Morbidity Percentage | Mortality Percentage |
|---|---|---|---|---|---|---|---|
| Acute | Water | 10X | 1 day | 0/5 | 0/5 | 0 | 0 |
| Acute | Weight loss formula | 10X | 1 day | 0/5 | 0/5 | 0 | 0 |
| Chronic | Water | 5X | 14 days | 0/5 | 0/5 | 0 | 0 |
| Chronic | Weight loss formula | 5X | 14 days | 0/5 | 0/5 | 0 | 0 |

|  | BUN (mg/dL) | Alanine aminotransferase (U/L) | White blood cells (10^3/µL) | Red blood cells (10^6/µL) | Hemoglobin (g/dL) | Platelets (10^3/µL) | neutrophils (10^3/µL) | lymphocytes (10^3/µL) | eosinophils (10^3/µL) | Basophils (10^3/µL) |
|---|---|---|---|---|---|---|---|---|---|---|
| Water | 27.0±2.8 | 27.5±18.6 | 6.6±3.1 | 8.6±3.5 | 13.7±1.0 | 1155.8±706.8 | 2920.5±1247.2 | 3346.0±2248.2 | 63.8±82.1 | 0.0±0.0 |
| WL | 21.0±4.4 | 33.0±5.4 | 6.0±3.5 | 8.1±0.6 | 12.9±0.8 | 1056.2±526.3 | 2233.4±1692.3 | 3496.2±1763.0 | 52.0±71.3 | 0.0±0.0 |
| Reference | 14-32 | 16-58 | 5.4-16.0 | 6.7-9.71 | 10.2-16.6 | 799-1300 | 1900-3600 | 2900-10000 | 0-500 | 0-400 |

Fig 8

WEIGHT LOSS FORMULATIONS, METHODS, AND COMPOSITIONS BASED ON TRADITIONAL CHINESE MEDICINE

CROSS-REFERENCE TO RELATED APPLICATIONS

This application is a §371 national phase of PCT Application PCT/US2014/068396, filed on Dec. 3, 2014, which claims priority to U.S. Provisional Application No. 61/911,041, filed on Dec. 3, 2013, the contents of each of which are incorporated herein by reference.

STATEMENT REGARDING FEDERALLY SPONSORED RESEARCH

N/A

FIELD OF THE INVENTION

The present invention relates to weight loss formulations, methods and compositions.

INCORPORATION BY REFERENCE OF SEQUENCE LISTING

The Sequence Listing in the ASCII text file, named as 33560_SEQ_ST25.txt of 2 KB, created on Mar. 16, 2017, and submitted to the United States Patent and Trademark Office via EFS-Web, is incorporated herein by reference.

BACKGROUND OF THE INVENTION

In the past 20 years, the worldwide prevalence of obesity has more than doubled. In 2008, more than 1.4 billion adults were overweight. (1) Using the definition of obesity as a body mass index (BMI) greater than or equal to 30, over 200 million of these men and nearly 300 million of these women were defined as obese (1). The National Health and Nutrition Examination Survey revealed that more than one-third of adult Americans were obese in 2009-2010. (2) It is projected that obesity prevalence rates for the United States will be more than 40% by 2025. (3) Obesity is a chronic disease associated with significant morbidity, and has substantial healthcare implications, due to increased risk for diseases including hypertension, diabetes, stroke, inflammation disorders and certain cancers (3;4). Overweight and obesity rank as the fifth leading risk for death globally. (1) At least 2.8 million adults worldwide die each year in part due to being overweight or obese. (1) These data demonstrate the major public health challenge of obesity.

The standard treatment for obesity is diet, exercise and behavior modification. More than two-thirds of adults in the United States are either trying to lose weight or to maintain their weight. However, only 20 percent are both eating fewer calories and engaging in at least 150 minutes of physical activity per week. (5) Therefore, lifestyle modification approaches have had low success rates and frequent relapses. Drug therapy has been utilized as an additional treatment component, although issues of efficacy and safety limit utilization. Current pharmacotherapies include orlistat and lorcaserin, as well as a number of sympathomimetic and antiepileptic drugs. The choice of anti-obesity drugs is often guided by the comorbidities and relative contraindications of the individual patient. Bariatric surgery is an appropriate option for a specific subset of patients, although this may result in serious complications. Due to the adverse effects of the prescription drugs for obesity and the potential complications of bariatric surgery, (6) there is increasing interest in herbal medications for weight loss. Over the counter dietary supplements are widely used by individuals attempting to lose weight, but evidence supporting their efficacy is lacking. As reviewed by Manore in 2012, (7) most dietary supplements only resulted in less than 2 kilogram (2-3%) weight loss in adults. Certain imported dietary supplements have been found to be adulterated with prescription drugs, including amphetamines, benzodiazepines, and fluoxetine, which has led to an FDA warning against their use. (8)

Weight Loss tea 1 ("WL-1") is a 6-herb formulation, composed of traditional Chinese Medicines (TCM) used for weight loss in TCM practice. (9) All medicinal herbs in this formula have been documented to be safe and reported to have clinical effects on obesity (9;10). However, evidence based studies of reputed weight loss effects are lacking Rodent models of high-fat-diet (HFD) induced obesity are important research tools that provide a window into disease pathogenesis and useful preclinical models for obesity treatment. (11) We evaluated the safety and efficacy of WL-1 in a mouse model of HFD induced obesity. The effects of WL-1 on body weight, food consumption, epididymal fat tissue weights and PPARγ and FABP4 gene expression, and serum glucose and cholesterol levels were determined.

SUMMARY OF THE INVENTION

As specified in the Background Section, above, there is a great need in the art to develop new therapeutic tools for the treatment of obesity and/or the reduction of body fat in subjects.

Therefore, in one embodiment the invention of the present disclosure is a method for decreasing body weight in a subject comprising the step of administering a pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for augmenting weight loss in subjects on a reduced calorie diet comprising the step of administering a pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for suppressing weight gain in a subject on a high calorie diet comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for reducing epididymal adipose tissue weight in a subject comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for reducing fat, particularly visceral fat in a subject comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method of reducing serum cholesterol levels in a subject the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for reducing glucose levels in a subject comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for increasing epididymal fat PPARγ gene expression in a subject comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for increasing FABP4 gene expression in a subject comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for increasing epididymal fat PPARγ and FABP4 expression in a subject comprising the step of administering a pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

In another embodiment the invention of the present disclosure is a method for increasing CPT1, UCP2, and AMPK gene expression, either alone or in combination, comprising the step of administering an pharmacologically effective amount of a formulation comprising extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao).

BRIEF DESCRIPTION OF THE DRAWINGS

FIG. 8 show the safety and biochemical analysis of WL-1.

DETAILED DESCRIPTION OF THE INVENTION

Figure 1:
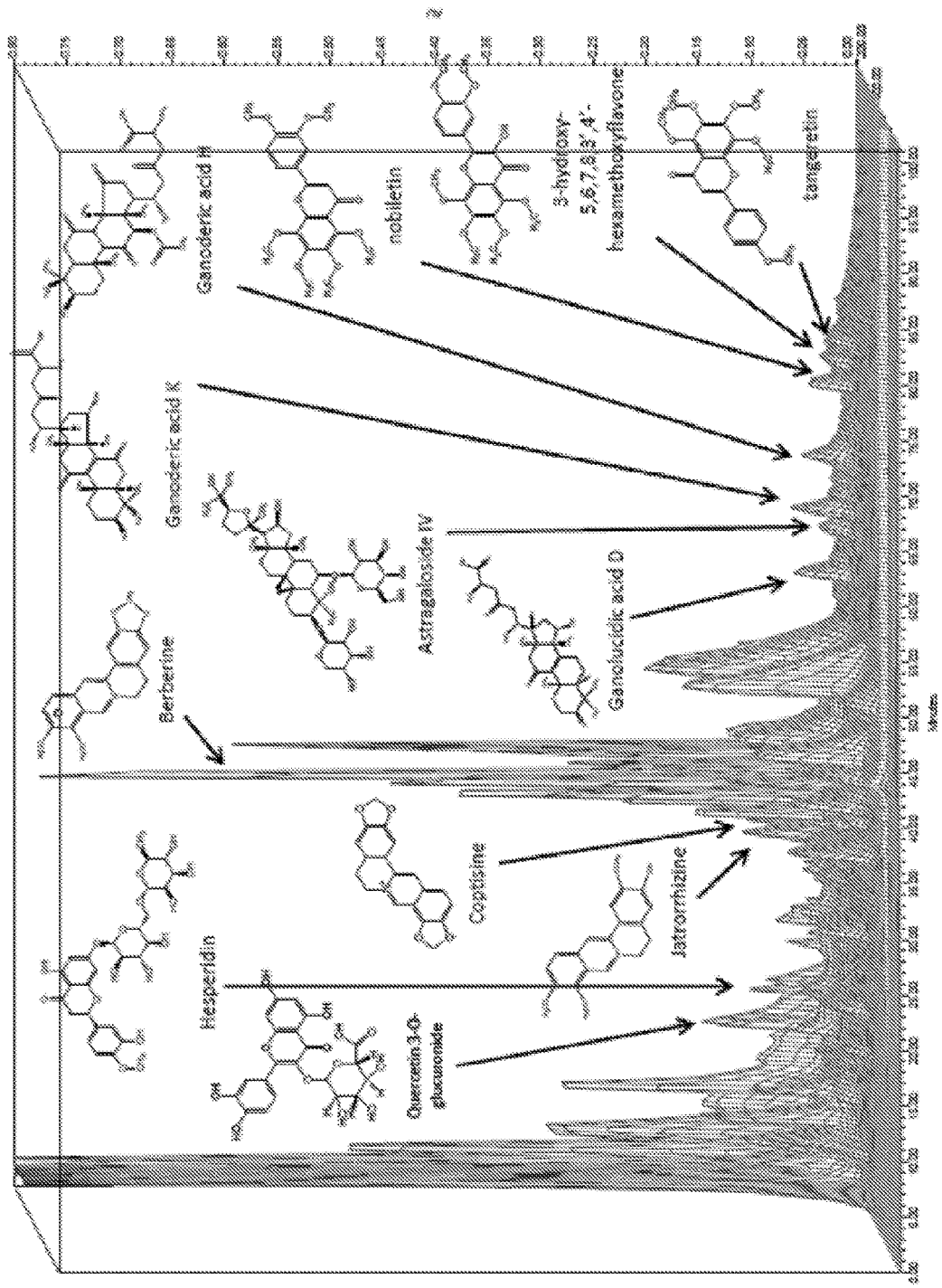
FIG. 1 shows an HPLC fingerprint of WL-1.

The present invention is based on the identification of certain natural products and extracts therefrom that have the capability of affecting the (i) reduction of body weight, (ii) rate of weight gain or loss, (iii) reduction of epididymal adipose tissue; (iv) reduction of fat, in particular visceral fat, (v) reduction of serum cholesterol levels, and (vi) reduction of glucose levels. The present inventors identified extracts of 6 Chinese medicinal herbs, *Ganoderma lucidum*, rhizome of *Coptis chinensis*, *Radix astragali*, *Nelumbo nucifera* Gaertn, *Chaenomeles speciosa*, and *Fructus aurantii*, administered in various combinations as effective at the above. Various experiments described in further detail below established the importance of these extracts for the previously mentioned purposes. Taken together the data demonstrate the therapeutic potential of these extracts.

While not being limited to any particular mechanism of action, the invention of the present disclosure may have its effect by affecting gene regulation. Specifically, treatment of a subject with the formulations described herein may alter the expression of the following genes, either alone or in combination: PPARγ, FABP4, CPT1, UCP2, and AMPK. Particularly, the expression of these genes, either alone or in combination may be increased. More particularly, the expression of these genes, either alone or in combination may be increased in adipose (fat) tissue, particularly epididymal adipose tissue.

Constituents

*Ganoderma lucidum*, a large, dark mushroom with a glossy exterior and a woody texture. The Latin word lucidus means "shiny" or "brilliant" and refers to the varnished appearance of the surface of the mushroom. In China, *G. lucidum* is called lingzhi, whereas in Japan the name for the Ganodermataceae family is reishi or mannentake.

Rhizome of *Coptis chinensis*, officially recognized in the Chinese Pharmacopoeia as *Coptidis Rhizoma*, (CR), also known as Huang Lian, and frequently found in traditional Chinese herbal formulae have been reported to exert a number of pharmacological actions.

*Radix astragali*, is cylindrical, some upper branches relatively thick, 30-90 cm long, 1-3.5 cm in diameter. Externally pale brownish yellow or pale brown, with irregular, longitudinal wrinkles or furrows. Texture hard and tenacious, broken with difficulty, fracture highly fibrous and starchy, bark yellowish white, wood pale yellow, with radiate striations and fissures, the centre part of old root occasionally looking like rotten wood, blackish brown or hollowed

*Nelumbo nucifera* Gaertn, also known as Indian lotus, sacred lotus, bean of India, or simply lotus, is one of two species of aquatic plant in the family Nelumbonaceae. The Linnaean binomial *Nelumbo nucifera* (Gaertn.) is the currently recognized name for this species, which has been classified under the former names, *Nelumbium speciosum* (wild.) and *Nymphaea nelumbo*, among others.

*Chaenomeles speciosa*, commonly known as flowering quince or Japanese quince or as zhou pi mugua in traditional Chinese medicine is a thorny deciduous or semi-evergreen shrub native to eastern Asia. It is taller than another commonly cultivated species, *C. japonica*, usually growing to about 2 m (6 ft 7 in). The flowers are usually red, but may be white or pink, and the fruit is a fragrant but hard pome that resembles a quince. In some embodiments of the invention this constituent is left out.

*Fructus aurantii*, also known as the Bitter Orange tree is native to eastern Africa and tropical Asia. Today, it is grown throughout the Mediterranean region and elsewhere, including California and Florida. Bitter orange oil is used in foods, cosmetics, and aromatherapy products. Bitter orange oil from the tree's leaves is called petitgrain, and oil from the flowers is called neroli. Bitter orange has been used in traditional Chinese medicine and by indigenous people of the Amazon.

Extraction Methods

In order to formulate pharmaceutically acceptable formulations, the constituent herbs are extracted either via an aqueous extraction, or an aqueous extraction followed by a butanol extraction.

W-LHIT: (also referred to as "WL-1" herein)

W-LHIT/WL-1 formulation was developed with dried aqueous extracts of 6 Chinese herbal medicines-*Ganoderma lucidum*, rhizome of *Coptis chinensis*, *Radix astragali*, *Nelumbo nucifera* Gaertn, *Chaenomeles speciosa*, and *Fructus aurantii*. All raw herbs are Chinese origin although the origin of the herbs is not critical. All herbs were extracted with water and then concentrated and dried according to a standard decocting and drying manufacturing process. Briefly, All herbs were cut into small pieces and soaked in 10 times volume of water overnight, and then boiled for 2 hours. The decoctions were collected and the residues were boiled with another 8 volumes of water for 2 hours two more times. All decoctions collected were combined and dried under reduced pressure. The dried production was ground into fine powder. The dried powder extract was packaged and stored at room temperature in a dry and well-ventilated botanical storage.

High pressure liquid chromatography (HPLC) fingerprinting was used as a means of standardization of botanical products. The HPLC fingerprint of W-LHIT was generated using a Waters 2690 HPLC coupled with photodiode array detector (PDA; Waters, Milford, Mass.). 100 mg of W-LHIT was dissolved into 1 ml of CH3CN and 0.1% formic acid mixture (1:1 ratio). The solution was filtered through Whatman 0.45 μm syringe filters (Whatman Inc., Clifton, N.J.). 10 μl of filtered solution was injected and analyzed on a ZORBAX SB-C18 (4.6×150 mm, 5 μm) column (Agilent, Santa Clara, Calif.). 0.1% aqueous formic acid was used as mobile phase A and CH3CN was used as mobile phase B with a constant flow rate of 1.0 mL/min. The gradient was started at 2% B and linearly went up to 25% B within 45 min, then to 35% B within 25 min, to 55% B within 15 min, to 75% B within 10 min, and maintained at 75% B for 5 min. Waters' Empower software was used for data collection and analysis. A total of 21 major peaks were present in the HPLC fingerprint (FIG. 1). Twelve compounds were characterized by Liquid chromatography-mass spectrometry (LC-MS) as quercetin 3-O-glucuronide from *Nelumbo nucifera* Gaertn; hesperidin, nobiletin, tangeretin, and 3-hydroxy-5,6,7,8,3',4'-hexamethoxyflavone from *Fructus aurantii*; jatrorrhizine, coptisine, and berberine from rhizome of *Coptis chinensis*; astragaloside IV from *Radix astragali*; ganolucidic acid D, ganoderic acid K, and ganoderic acid H from *Ganoderma lucidum*. Three batches of W-LHIT products were generated. HPLC fingerprints of each individual herbal medicine and comparison of peak intensities of identified compounds were used to monitor the quality of different batches of W-LHIT product. Berberine was used as the key index compound.

W-LHIT-B:

W-LHIT-B was formed from the same constituent herbs as W-LHIT serially extracted with water followed by butanol. Butanol extracts of W-LHIT (W-LHIT-B) were prepared in the laboratory. 10 g of W-LHIT formula was ground into fine powder and dissolved into 200 mL of DDH2O. Equal volume of Butanol was fully mixed with the W-LHIT solution and the mixture was transferred into a separatory funnel. Separated butanol extracts were collected. The butanol extract was then mixed with distilled water (3:1 ratio) and evaporated under reduced pressure using a Rotary evaporator. The dried extract (W-LHIT-B) was stored at room temperature.

W-LHIT-C:

W-LHIT-C was formed from the same constituent herbs as W-LHIT with the *Chaenomeles speciosa* not present, serially extracted with water followed by butanol. This formula was generated by combination of butanol extracts of rhizome of *Coptis chinensis* (about 30-90% *Radix astragali* (about 0.5-20%) *Fructus Aurantii* (about 0.5%-20%), *Ganoderma lucidum* (about 0.5-40%), and *Nelumbo nucifera* Gaertn (about 0.5-20%). Each individual herbal component was extracted using butanol from the dried aqueous extract and dried under vacuum. The yield was 25%, 11.6%, 31.6%, 12%, and 32.5% respectively.

Definitions

In the context of the present invention insofar as it relates to any of the disease conditions recited herein, the terms "treat", "treatment", and the like mean:
  a. preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or
  b. inhibiting the state, disorder or condition, i.e., arresting, reducing or delaying the development of the disease or a relapse thereof (in case of maintenance treatment) or at least one clinical or sub-clinical symptom thereof; or c. relieving the disease, i.e., causing regression of the state, disorder or condition or at least one of its clinical or sub-clinical symptoms.

As used herein the term "therapeutically effective" applied to dose or amount refers to that quantity of a compound, plurality of compounds, extract or plurality of extracts, (e.g., extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao)) or pharmaceutical composition that is sufficient to result in a desired activity upon administration to an animal in need thereof. Within the context of the present invention, the term "therapeutically effective" refers to that quantity of a compound, plurality of compounds, extract or plurality of extracts or pharmaceutical composition that is sufficient to reduce or eliminate at least one symptom of a disease specified above. Note that when a combination of active ingredients is administered (e.g., extracts of *Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao)), the effective amount of the combination may or may not include amounts of each ingredient that would have been effective if administered individually. Therapeutically effective dosages according to the present invention can be determined stepwise by combinations of approaches such as, e.g., (i) reduction of body weight, (ii) rate of weight gain or loss, (iii) reduction of epididymal adipose tissue; (iv) reduction of fat, in particular visceral fat, (v) reduction of serum cholesterol levels, (vi) reducing glucose levels, (vii) levels of PPARγ and FABP4 gene expression, either alone or in combination, (viii) levels of CPT1, UCP2, and AMPK gene expression either alone or in combination.

The phrase "pharmaceutically acceptable", as used in connection with the compositions and/or formulations of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "subject" means any animal, including mammals and, in particular, humans.

As used in this specification and the appended claims, the singular forms "a," "an," and "the" include plural references unless the context clearly dictates otherwise.

In accordance with the present invention, there may be employed conventional pharmacology, medicinal chemistry, molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

Pharmaceutical Compositions of the Invention

For administration to human and animal patients, compounds and extracts, of the present invention can be formulated in pharmaceutical compositions in combination with one or more pharmaceutically acceptable carriers and/or excipients such as, e.g., lubricants, diluents, flavorants, colorants, buffers, and disintegrants. Suitable pharmaceutically acceptable carriers include any and all conventional solvents (such as, e.g., water, physiological solution, dextrose, glycerol, ethanol, and the like, as well as combinations thereof), wetting agents, emulgators, buffers, conservants, dispersion media, fillers, solid carriers, aqueous solutions, coatings, antibacterial and antifungal agents, isotonic and absorption delaying agents, as well as other well-known agents which enhance the shelf life or effectiveness of one or more of the active components of the composition. Examples of such useful substances can be found in "Remington's Pharmaceutical Sciences" by E. W. Martin. Except insofar as any conventional media or agent is incompatible with the active ingredient, use thereof in compositions of the present invention is contemplated. The term "pharmaceutically acceptable" refers to a carrier or excipient that does not cause an allergic reaction or other untoward effect in patients to whom it is administered.

The pharmaceutical compositions of the invention can be produced in useful dosage units for administration by various routes including, among others, topical, oral, subcutaneous, intravenous, and intranasal administration.

The pharmaceutical compositions of the invention can also include other biologically active substances in combination with the formulations, individual constituents of the formulations and/or isolates thereof of the invention. Such additional biologically active substances can be also formulated as separate compositions and can be administered simultaneously or sequentially with the formulations, individual constituents of the formulations and/or isolates thereof of the invention. Non-limiting examples of useful biologically active substances include statins, niacin, bile-acid resins, fibric acid derivatives, cholesterol absorption inhibitors, and other lipid-lowering drugs.

Administration

With the aid of present disclosure, those of skill in the art should be able to derive suitable dosages and schedules of administration for any of a number of suitable compositions that contain the compounds, extracts and formulations of the invention. Thus, pharmaceutical compositions within the scope of the present invention include compositions where the active ingredient(s) is contained in an effective amount to effect a (i) reduction of body weight, (ii) rate of weight gain or loss, (iii) reduction of epididymal adipose tissue; (iv) reduction of fat, in particular visceral fat, (v) reduction of serum cholesterol levels, (vi) reduction of glucose levels, (vii) levels of PPARγ and FABP4 gene expression, either alone or in combination, (viii) levels of CPT1, UCP2, and AMPK gene expression either alone or in combination.

The formulation and dose for therapeutic administration of the compounds formulations and extracts of the invention will depend on the severity of the disease condition being treated, whether other drugs are being administered, whether other actions are taken, the weight, age, and sex of the subject, and other criteria. The skilled medical practitioner will be able to select the appropriate formulation and dose in view of these criteria and based on the results of published clinical trials. The dosage and administration regimen can be further adjusted for an individual patient by monitoring the various physiological indicia described above.

The optimal therapeutically effective amount of compounds formulations and extracts of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

As disclosed herein, the concentrations of the formulations administered in the present invention are both therapeutically effective and pharmaceutically acceptable. The compounds, extracts and formulations of the present invention are preferably used in vivo at the following dose ranges:

In various embodiments and formulations, the individual constituent extracts will be present in the following amounts/weight percents:

*Ganoderma lucidum* (Ling Zhi) from about 0.5-40%, particularly about 0.5-20%, and more particularly about 0.5-10%

Rhizome of *Coptis chinensis* (Huang Lian) from about 30-90%, particularly about 30-85%, and more particularly about 30-75%

*Radix astragali* (Huang Qi) from about 0.5-20%, particularly about 0.5-10%, and more particularly about 0.5-7%

*Nelumbo nucifera* Gaertn (He Yie) from about 0.5~20%, particularly about 0.5~10%, and more particularly about 0.5-5%.

*Chaenomeles speciosa* (Mu Gua) from about 0.5-20%, particularly about 0.5~10%, and more particularly about 0-0.5%. In some embodiments this constituent is not used in the formulations.

*Fructus Aurantii* (Zhi Qiao) from about 0.5-20%, particularly about 0.5-10%, and more particularly about 0.5-7%.

Following methodologies which are well-established in the art, effective doses and toxicity of the compounds formulations and extracts of the present invention, which performed well in in vitro tests, can be determined in studies using small animal models (e.g., mice, rats) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the compounds formulations and extracts in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compounds formulations and extracts of the invention can be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it can be expressed as the ratio ED50/LD50.

The compounds formulations and extracts of the invention can be formulated for parenteral, oral, topical, transdermal, transmucosal, intranasal, buccal administration, or by any other standard route of administration. Parenteral administration includes, among others, intravenous (i.v.), subcutaneous (s.c.), intraperitoneal (i.p.), intramuscular (i.m.), subdermal (s.d.), intradermal (i.d.), intra-articular, intra-synovial, intra-arteriole, intraventricular, intrathecal, intrasternal, intrahepatic, intralesional, or intracranial administration, by direct injection, via, for example, bolus injection, continuous infusion. A preferred route of administration according to the present invention will depend primarily on the indication being treated and includes, among others, topical, oral, subcutaneous, intravenous, and intranasal administration.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use. Suitable formulations for parenteral administration may contain substances which increase viscosity, for example, sodium carboxymethyl cellulose, sorbitol, and/or dextran. Optionally, the formulation may also contain stabilizers.

For oral administration, the compositions of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Delivery

Compositions of the present invention can be delivered systemically or locally. If targeted delivery to a particular cell or tissue is desirable, compounds and formulations may be coupled to conjugates or delivery vectors containing antibodies to cell- or tissue-specific antigens can be used.

Therapeutic Methods of the Invention

In conjunction with the novel compounds and compositions, provided herein are methods of treatment using such compounds and formulations. Specifically, the invention provides a method for treating a disease or condition in a subject in need thereof, which method comprises administering to the subject a therapeutically effective amount of one or more compounds formulations and extracts of the invention or a composition comprising such one or more compounds and compositions. Non-limiting examples of the diseases or conditions treatable by the method of the invention include obesity and the biological sequelae of obesity including but not limited to high cholesterol and high blood glucose.

While not being limited to any particular mechanism of action, the invention of the present disclosure may have its effect by affecting gene regulation. Specifically, the invention provides a method for altering the expression of the following genes, either alone or in combination: PPARγ, FABP4, CPT1, UCP2, and AMPK. Particularly, the expression of these genes, either alone or in combination may be increased. More particularly, the expression of these genes, either alone or in combination may be increased in adipose (fat) tissue, particularly epididymal adipose tissue.

In a preferred embodiment, the subject is mammal.
In a preferred embodiment, the subject is human.
Turning now to the figures FIG. 1. HPLC fingerprint of WL-1. HPLC conditions: column, Agilent Zorbax SB-C 18 column (150×4.6 mm i.d.; 5 μm particle size); flow rate, 1 mL/min; column temperature, 27° C.; mobile phase A, 0.1% formic acid, mobile phase B, acetonitrile. Data were processed using Waters Empower software. Twenty-one major peaks were present in the HPLC fingerprint. Eleven compounds were characterized by LC-MS.

Figure 2:
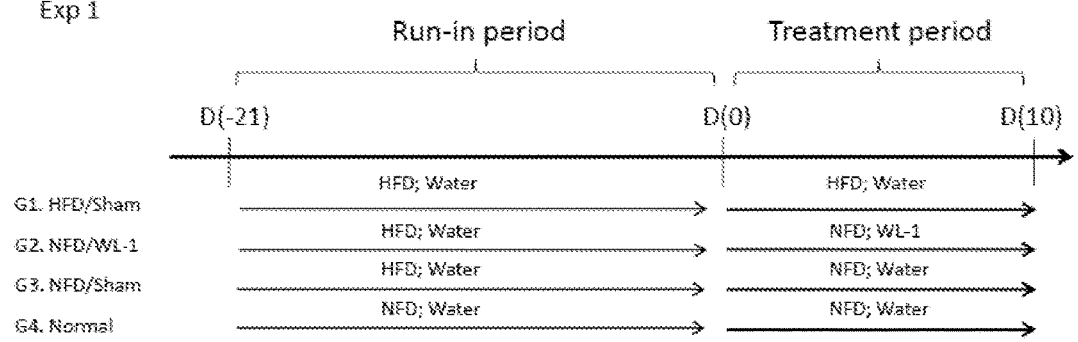
FIG. 2 shows the protocols of weight loss experiments 1 (A) and experiment 2 (B).
Figure 2:
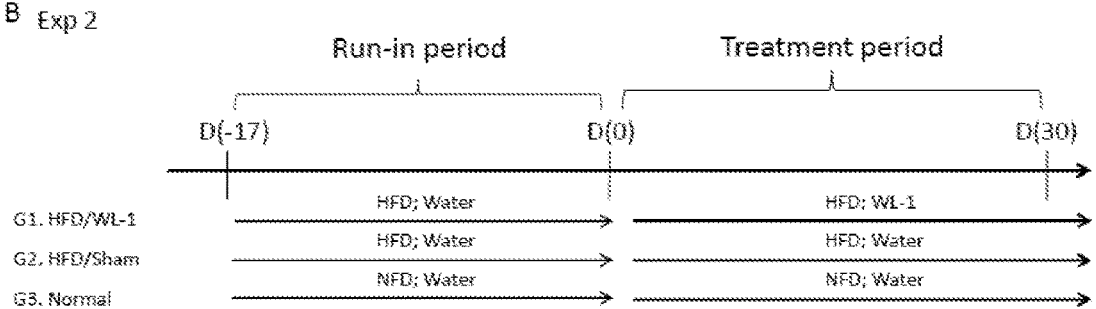

FIG. 2. Protocols of weight loss experiments 1 (A) and experiment 2 (B).

Figure 3:
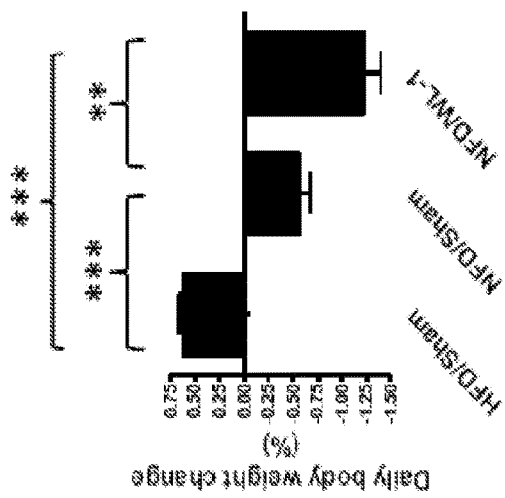
FIG. 3 shows the effect of WL-1 on young obese mice bodyweights.
Figure 3:
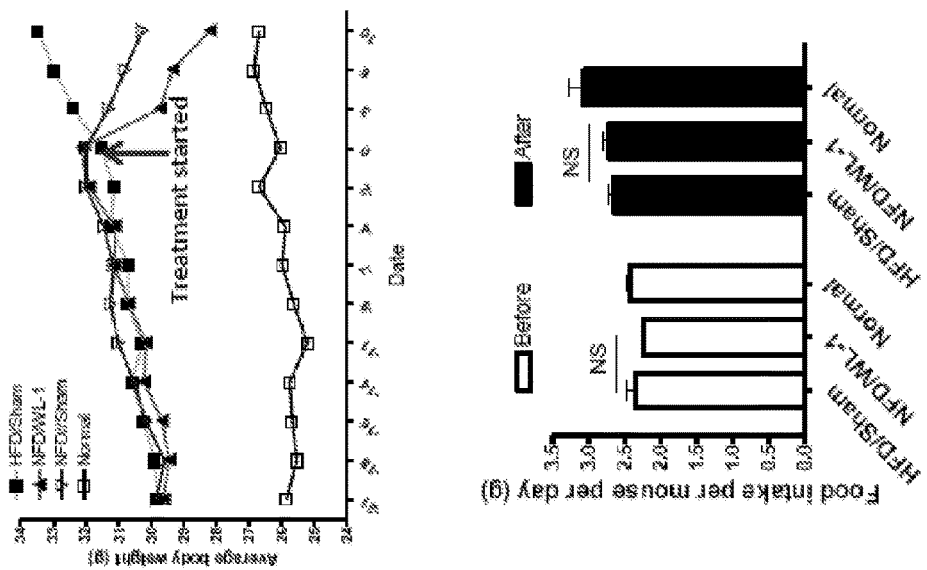

FIG. 3. Effect of WL-1 on young obese mice bodyweights in experiment 1. A. Average body-weight change curve of sham and WL-1 treated obese mice over time; B. daily body weight change; C. Daily food consumption per mouse; $p<0.01$; *$p<0.001$ (n=5). Data represent two independent experiments.

Figure 4:
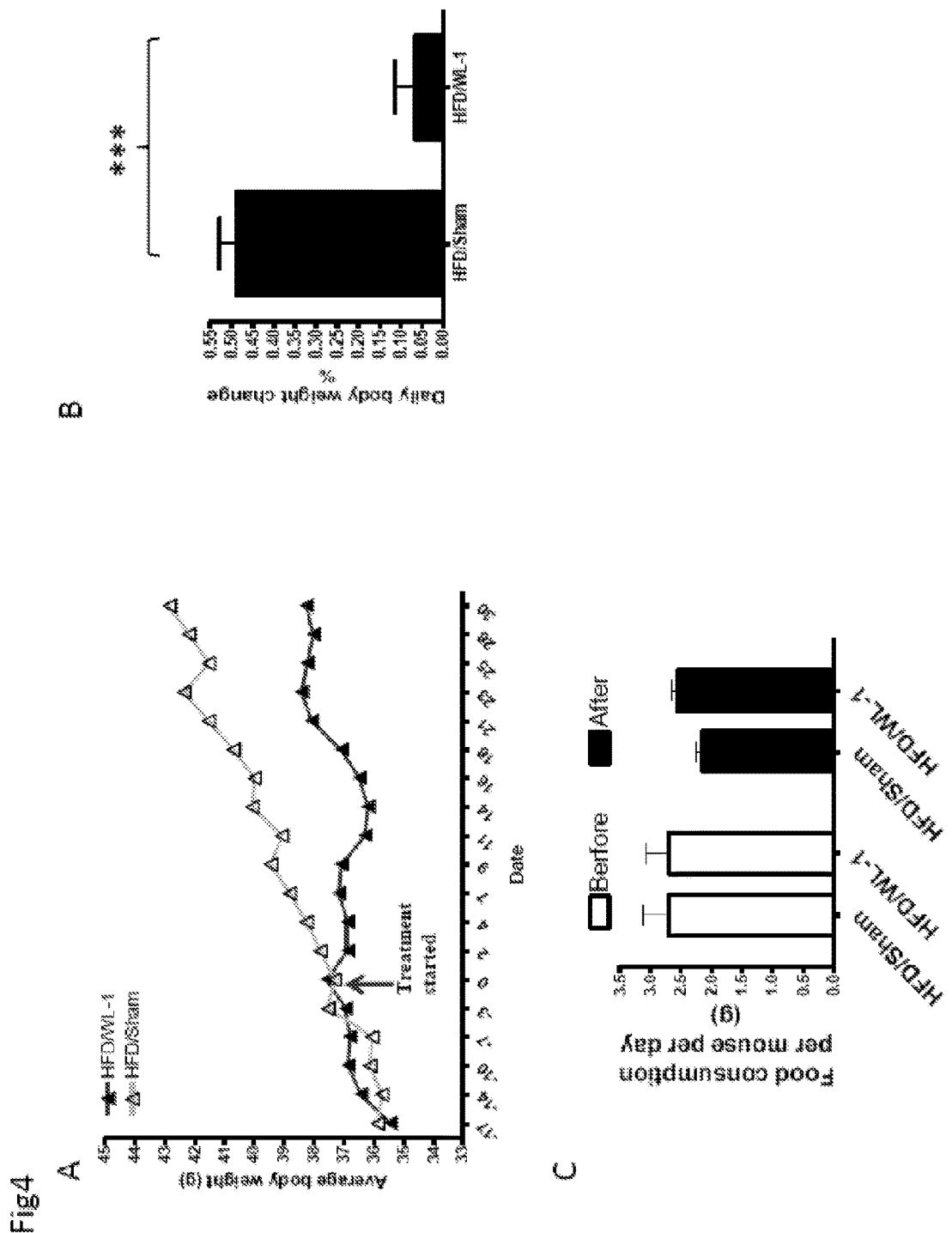
FIG. 4 shows the effect of WL-1 on body weights of older obese mice.

FIG. 4. Effect of WL-1 on body weights of older obese mice in experiment 2. A. Average body-weight change curve of sham and WL-1 treated obese mice; B. Daily body weight change before and after treatment; C. Daily food consumption per mouse; ***$p<0.001$ (n=5). Data represent two independent experiments.

Figure 5:
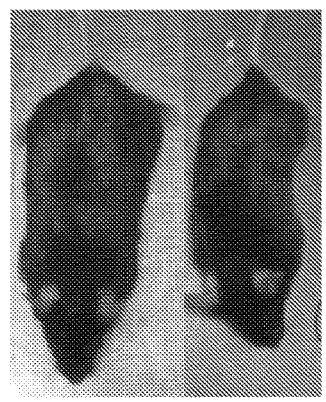
FIG. 5 shows the effect of WL-1 on epididymal fat tissue weights of older obese mice in experiment 2.
Figure 5:
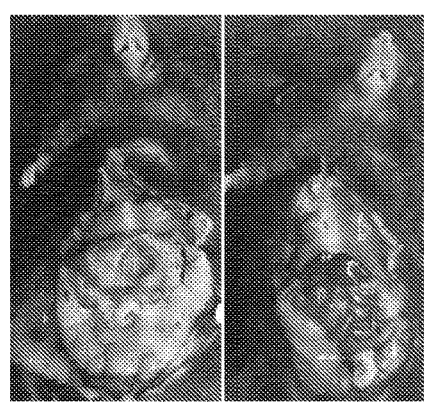
Figure 5:
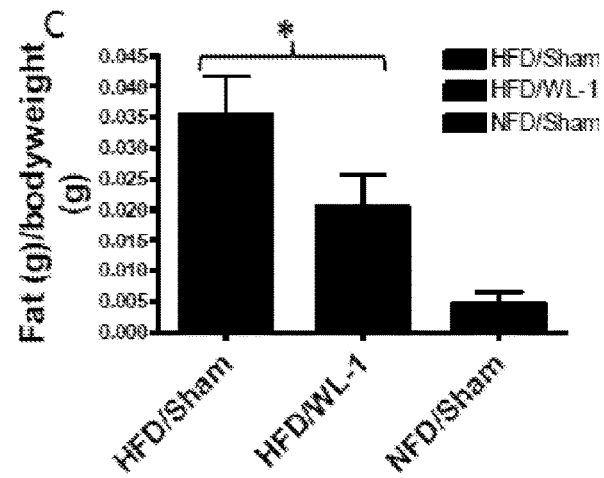

FIG. 5. Effect of WL-1 on epididymal fat tissue weights of older obese mice in experiment 2. A. Gross body shape of Sham (left) and WL-1 treated (right) mice; B. Abdominal fat in Sham (left) and WL-1 treated (right) mice; C. Epididymal fat per body weight. Data are expressed as Mean±S.D. *$p<0.05$ (n=5).

Figure 6:
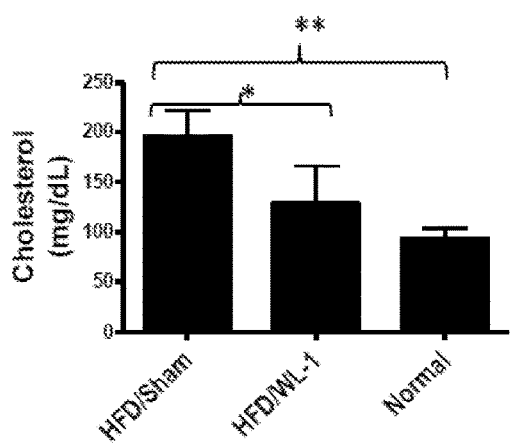
FIG. 6 shows the effect of WL-1 on blood cholesterol and glucose levels of older obese mice in experiment 2.
Figure 6:
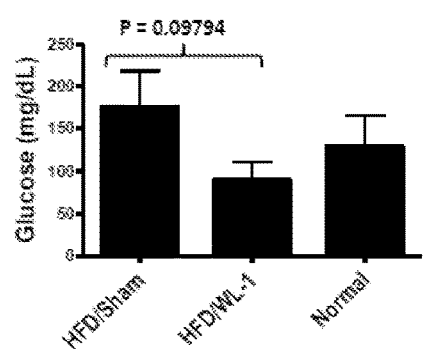

FIG. 6. Effect of WL-1 on blood cholesterol and glucose levels of older obese mice in experiment 2. A. Cholesterol levels and B. Glucose levels in WL-1 treated and sham-treated older obese mice and normal controls. Data are expressed as Mean±S.D. *$p<0.05$; **$p<0.01$ (n=4-5).

Figure 7:
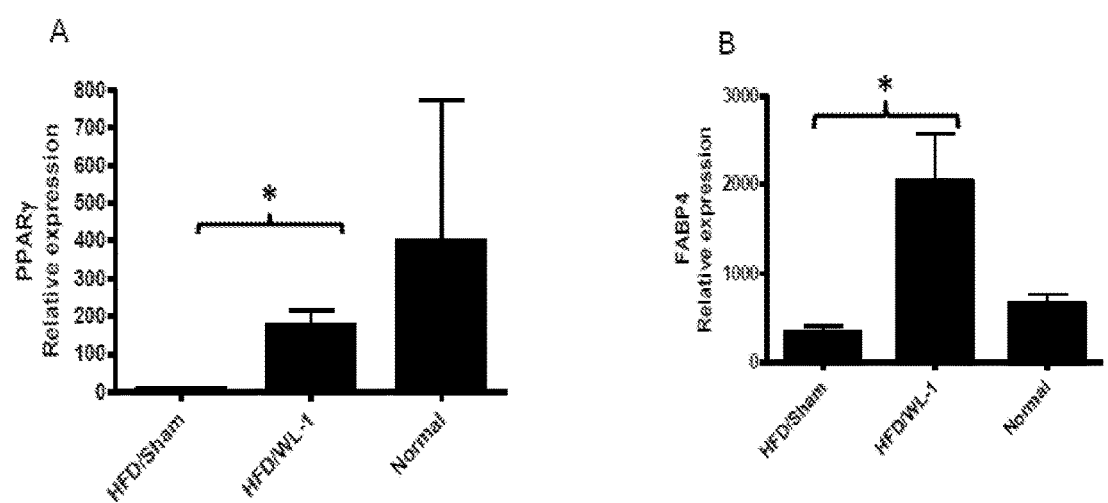
FIG. 7 shows real time PCR of epididymal adipose tissues PPARγ (A) and FABP4 gene expressions (B) in experiment 2.
Figures 8A, 8B, 8C:
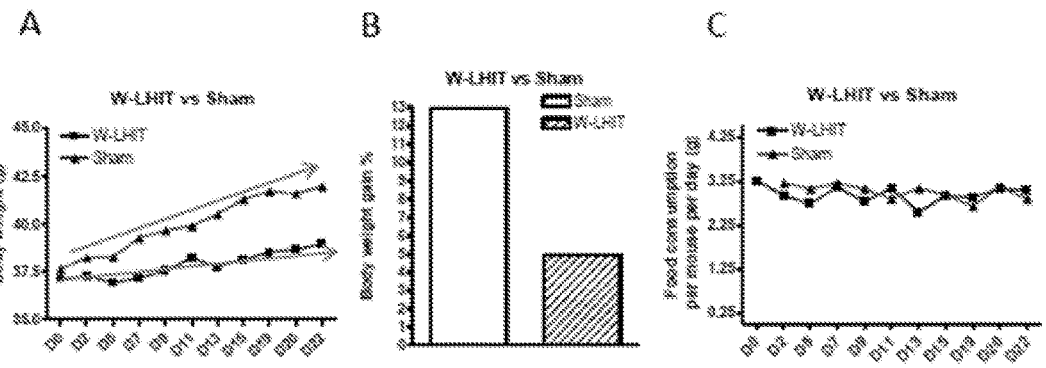
FIGS. 8A-8C. The effects of W-LHIT on body weight and food intake. (A) Body weight (g) of W-LHIT versus Sham treated mice over time (B) Body weight gain percentage of W-LHIT versus Sham treated mice (C) Food consumption per mouse per day(g) of W-LHIT versus Sham treated mice over time.

FIG. 7. Real time PCR of epididymal adipose tissues PPARγ (A) and FABP4 gene expressions (B) in experiment 2. Data expressed as Mean±S.D. *$p<0.05$ (n=4-5). group) fed a chow diet.

FIGS. 8A-8C, 9A-9C and 10A-10C show the effects on bodyweight over time, percent body weight gain, and food intake of W-LHIT, W-HLIT-B, and W-LHIT-C respectively.

EXAMPLES

The present invention is further described by way of the following particular examples. However, the use of such examples is illustrative only and is not intended to limit the scope or meaning of this invention or of any exemplified term. Nor is the invention limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

Example 1

Methods:
Mice and Reagents

Fourteen-week-old high-fat-diet induced obese and normal chow fed C57BL/6J mice were purchased from the Jackson Laboratory (Bar Harbor, Me.). These mice were maintained under specific pathogen-free conditions according to standard guidelines for the care and use of animals (12). The study protocol was approved by Institutional Animal Care and Use Committee at Icahn Mount Sinai School of Medicine, New York. HFD chow, prepared by Research Diets, Inc. (New Brunswick, N.J.), was composed of 20 kcal % protein, 35 kcal % carbohydrate, and 45 kcal % fat. Normal fat diet (NFD, Purina #5053, St. Louis, Mo.), was composed of 23 kcal % protein, 64 kcal % carbohydrate, and 11 kcal % fat.

WL-1 Preparation and Quality Control:

WL-1 (Blue Light, Inc. Ithaca, N.Y.) formulation contains dried aqueous extracts of 6 Chinese herbal medicines-*Ganoderma lucidum* (Ling Zhi), rhizome of *Coptis chinensis* (Huang Lian), *Radix astragali* (Huang Qi), *Nelumbo nucifera* Gaertn (He Yie), *Chaenomeles speciosa* (Mu Gua), *Fructus Aurantii* (Zhi Qiao). All raw herbs are Chinese origin, which was certified and individually extracted by a good manufacturer product (GMP) facility, Tian Jiang pharmaceutical Co, Ltd, Jiangsu, China. (13) All herbs were extracted with water and then concentrated and dried according to the standard decocting and drying manufacturing process. (13) The dried powder extract was packaged and stored at room temperature in a dry and well-ventilated botanical storage room at Botanical Chemistry Laboratory at Icahn School of Medicine at Mount Sinai. The tests for heavy metal and microbial content was conducted by Tianjian Pharmaceutical Ltd. Jiangsu, China and the results met required standards (10;14-17)

High pressure liquate chromatograph (HPLC) fingerprinting is recommended by the FDA as a means of standardization of botanical products. The HPLC fingerprint of WL-1 was generated using a Waters 2690 HPLC coupled with photodiode array detector (PDA; Waters, Milford, Mass.). 100 mg of WL-1 was dissolved into 1 ml of CH 3 CN and 0.1% formic acid mixture (1:1 ratio). The solution was filtered through Whatman 0.45 μm syringe filters (Whatman Inc., Clifton, N.J.). 10 μL of filtered solution was injected and analyzed on a ZORBAX SB-C18 (4.6×150 mm, 5 μm) column (Agilent, Santa Clara, Calif.). 0.1% aqueous formic acid was used as mobile phase A and CH 3 CN was used as mobile phase B with a constant flow rate of 1.0 mL/min. The gradient was started at 2% B and linearly went up to 25% B within 45 min, then to 35% B within 25 min, to 55% B within 15 min, to 75% B within 10 min, and maintained at 75% B for 5 min. Waters' Empower software was used for data collection and analysis. A total of 21 major peaks were present in the HPLC fingerprint (FIG. 1). Eleven compounds were characterized by Liquid chromatography-mass spectrometry (LC-MS) as quercetin 3-O-glucuronide, hesperidin, nebiletin, 3-hydroxy-5,6,7,8,3',4'-hexamethoxyflavone, jatrorrhizine, coptisine, berberine, astragaloside IV, ganolucidic acid D, ganoderic acid K, and ganoderic acid H. Their chemical structures and corresponding peaks are shown in FIG. 1.

WL-1 Treatment

Each mouse received 84 mg WL-1 daily, dissolved in 1.0 ml drinking water, and intragastrically (i.g.) administered by two separate feedings (0.5 ml per feeding 4 hours apart using a standard mouse feeding needle (VWR, Radnor, Pa.). The WL-1 dose was determined by a conversion table of equivalent human to animal dose (18). We employed two protocols in two sets of experiments to determine the effect WL-1 on weight control as follows:

The first set of experiments was designed to determine the effect of WL-1 on weight loss as add-on therapy to dietary calorie reduction on young mice. In this set of experiments, three groups of age matched 14 week-old mice (equivalent to human age of 19 years) were first sham treated by i.g. administration of water while continuing on the HFD for 3 weeks. This protocol was used to acclimatize mice to i.g. administration to prevent potential gavage procedure effect on weight changes (run-in period). Sham treated normal weight mice (G4) fed a NFD served as normal controls. Three weeks later, all mice were weighed. Group 1 obese mice continued on HFD and sham treatment as the obesity control group (HFD/Sham). Both group 2 and 3 obese mice were switched from HFD to NFD, but group 2 mice received WL-1 (NFD/WL-1) whereas group 3 mice received water sham treatment (NFD/Sham). Group 4, the normal weight mice continued on NFD and water sham treatment, served as normal controls (Normal). Treatment duration was 10 days (FIG. 2 A).

Experiment 2: to determine the effect of WL-1 on HFD-induced weight gain in older mice, 14 week-old mice were maintained in animal facility at Icahn School of Medicine at Mount Sinai for 9 weeks on HFD until 23 weeks old (equivalent to roughly 40 year old human age). They were then subjected to 2 week acclimatization by i.g. water administration. These 25 week-old obese mice were divided into 2 weight matched groups (FIG. 2B). Group 1 mice continued on HFD and sham treatment as obese controls (HFD/Sham) while group 2 mice continued on HFD and received WL-1 treatment (HFD/WL-1). Treatment duration was 30 days. Normal weight mice fed with NFD and water sham treatment were used as normal controls (Normal).

Body weight and food consumption amounts were recorded three times a week. Body weight gain was calculated by subtracting body weight on the first day from that on the last day of treatment. Daily body weight gain was calculated by dividing body weight gain by the number of treatment days. Chow was weighed three times a week during the period of acclimatization and treatment, and daily food consumption was calculated by dividing total food consumption by the number days.

Biochemical Analysis

In experiment 2, mice were fasted overnight after 30 days of treatment and submandibular blood samples were collected. Sera were separated and stored at −80° C. for further analysis. The mice were sacrificed and tissues were harvested, weighed, and stored at −80° C. for further analysis. Serum cholesterol and glucose levels were measured by ALX Laboratories (New York, N.Y.). Since experiment 1 was a preliminary study designed to determine whether WL-1 as add-on therapy enhances normal diet intervention weight loss in young obese mice, we did not pursue biochemistry analysis for serum cholesterol and glucose levels in experiment 1.

RT-PCR

Epididymal fat pads was collected and weighed from mice in experiment 2. Total RNA was extracted from epididymal fat tissue using Trizol reagent (Life Technologies, Grand Island, N.Y.) according to the manufacturer's instruction. The concentrations of total RNA were measured using optical density (OD) readings (Bio-Rad SmartSpect 3000; Bio-Rad, Hercules, Calif.). cDNA was then synthesized using ImProm-II™

Reverse Transcriptase Kit (Promega Corporation, Madison, Wis.) following the manufacturer's instruction. The real time-PCR reaction was performed by using Maxima™ SYBR Green qPCR Master Mix (2×) kit (Fermentas, Glen Burnie, Md.). PCR was started at 95° C. for 10 minutes followed by 40 cycles. The temperature profile of each cycle was: 95° C. for 15 seconds, 60° C. for 30 seconds, and 72° C. for 30 seconds. The following primers were used: PPARγ forward: TTTCAAGGGTGCCAGTTT (SEQ ID NO: 1); PPARγ reverse: GAGGCCAGCATCGTGTAG (SEQ ID NO: 2); FABP4 forward: AAATCACCGCAGACGACA (SEQ ID NO: 3); FABP4 reverse: CACATTCCACCACCA-GCT (SEQ ID NO: 4). Gusb forward: 194 AGTATG-GAGCAGACGCAATC (SEQ ID NO: 5); Gusb reverse: CTCTCCGACCACGTATTCTT (SEQ ID NO: 6). All primers were synthesized by Sigma-Aldrich Corporation (St. Louis, Mo.).

Safety Testing

For acute toxicity analysis, naive mice were fed with 10 times the daily therapeutic dose for mice of WL-1 and observed for 14 days. In the sub-chronic toxicity assay, naive mice were fed 5 times their daily therapeutic dose for 14 days. Sham fed mice served as controls (sham). Blood samples were collected after each experiment. Blood urea nitrogen (BUN) and alanine aminotransferase (ALT) measurements for evaluation of kidney and liver functions respectively and complete blood count (CBC) testing were performed by ALX laboratories, NY.

Statistical Analysis

Data were analyzed using SigmaStat 3.5 software (SPSS Inc. Chicago, Ill.). For data that passed normality testing, differences between groups were analyzed by One Way Analysis of Variance (One way ANOVA) followed by pair wise testing using Bonferroni's adjustment. For data that appeared skewed (non-normal), differences between groups were analyzed by One Way ANOVA on Ranks followed by all pair wise comparisons. P values≤0.05 were considered significant.

Results

WL-1 treatment augmented young obese mice weight loss after switching to a reduced calorie diet. In the first set of experiments, we determined the effect of combined interventions on young obese mice by switching from HFD to NFD chow and adding WL-1 treatment. During the period of 3-week acclimatization, all mice on HFD continued to gain essentially the same amount of body weight (FIG. 3A, from days −21 to 0). During the 10-day treatment period, sham treated obese mice remaining on HFD continued to gain weight, 6.1±1.0% by day 10. However, obese mice switched to NFD receiving sham treatment (NFD/sham) lost 2.1±1.4% of body weight by day 3, 3.6±2.5% by day 5, and 5.5±2.8% by day 10. Interestingly, obese mice switched to NFD who also received WL-1 treatment lost weight more rapidly. Mice in this group lost 7.6±1.5% of their body weight by day 3, 8.7±2.7% by day 6, and 12.2±3.8% by day 10, (FIG. 3A). The calculated daily body weight changes over 10-day treatment period showed that body weight increased 0.6±0.1% daily in the HFD/Sham group, but decreased 0.5±0.3% daily in NFD/Sham group, and decreased 1.2±0.4% daily in NFD/WL-1 group. The daily reduction rate in NFD/WL-1 mice was 2.4 fold greater than NFD/Sham mice (p<0.05) (FIG. 3B). Daily chow consumption did not differ between WL-1 treated and Sham treated NFD chow intervention groups.

WL-1 suppressed weight gain in HFD fed older obese mice. In experiment 2, we determined the effect of WL-1 on 25 week-old male obese C57BL/6J mice. After the run-in period, mice were divided into 2 groups of equal body weight. Thirty days after initiating treatment, sham treated mice body weight increased by 14.6±2.8% while on HFD (HFD/sham). In contrast, WL-1 treated obese mice (HFD/WL-1) increased body weight by only 1.9±3.3% (FIG. 4A). Daily weight gain in the HFD/Sham group was 0.49±0.09% whereas daily weight gain in HFD/WL-1 group mice was only 0.06±0.10% (FIG. 4B, p<0.001), approximately 8 fold less than sham treated mice. NFD control mice daily weight 240 gain was 0.09±0.06% (data not shown). Food intake did not differ between WL-1 treated and sham-treated mice while on HFD (FIG. 4C).

WL-1 reduced epididymal adipose tissue weight in HFD fed older obese mice. After 30 days on HFD in experiment 2, sham treated mice body size increased, and they contained more visceral fat (FIG. 5A). WL-1 treated mice contained less visceral fat (FIG. 5B) and the amount of epididymal adipose tissue was 42% less than in sham treated mice (FIG. 5C, p<0.05).

WL-1 reduced serum cholesterol and glucose levels in HFD fed older mice. In experiment 2, after 30 days of treatment, mice were fasted overnight, and blood samples were collected. Serum cholesterol and glucose levels were measured. Mice in HFD/Sham group showed significantly increased serum total cholesterol levels than NFD normal controls (195.0±26.8 vs 93±11 mg/dL, p<0.01 FIG. 6A). Cholesterol levels in HFD/WL-1 group (128.5±37.6 mg/dL) were significantly lower than sham treated mice (p<0.05) and were not statistically different from the NFD normal controls (FIG. 6A). Blood glucose levels in HFD/WL-1 mice were also lower than that in HFD/Sham mice (90.5±39.6 mg/dL vs. 176.0±72.4 mg/dL, p=0.09), and were not different from NFD normal mice (121.7±62.2 mg/dL, p=0.35) (FIG. 6B).

WL-1 increased epididymal fat PPARγ and FABP4 expression in HFD fed older mice. Total mRNA was extracted from epididymal fat tissues of sham treated, WL-1 treated, and normal control mice in experiment 2, and PPARγ and FABP4 mRNA expression were analyzed using real time PCR. WL-1 treatment significantly increased the expression of PPARγ (p<0.05, FIG. 7A) and FABP4 (p<0.05, FIG. 7B). We also analyzed CPT1, UCP2, and AMPK gene expression, which are related to fat oxidation and metabolism. The results showed that the relative gene expressions of CTP1, UCP2, and AMPK in WL-1 treated mice also trended upward compared to that in sham treated mice (CTP1, 14.7±12.6 vs. 1.14±0.7; UCP2, 83.8±82.6 vs. 2.2±3.1; and AMPK, 19.1±15.5 vs. 0.2±0.3). However, these increases did not reach statistical significance.

WL-1 had a high safety profile. The safety of WL-1 was tested using 2 protocols. In an acute toxicity assay, mice were fed ten times the WL-1 treatment dose and observed daily for 14 days. No deaths occurred, and no abnormal behavior or diarrhea was observed (Table I). In a chronic toxicity assay, mice were fed 5 times the WL-1 treatment dose for 14 consecutive days. No diarrhea or deaths was observed, and all mice appeared healthy. Mice were then sacrificed and blood samples were obtained.

Serum ALT and BUN levels were similar to the control group and within the normal range (Table I). CBC testing was also performed and white blood cell, red blood cell, hemoglobin and platelet levels in the treated group were also within the normal range and similar to the control group (Table I). These results demonstrated that WL-1 formula has a high safety profile.

Discussion

Obesity is a growing concern worldwide, and conventional therapies thus far have proved limited. In this study, we examined the effects of WL-1, a natural product based on TCM, on HFD-induced obese mice using a previously employed C57BL/6J murine model fed a 45% kcal HFD (19). In the first experiment, mice lost body weight when switched from a HFD to a NFD. Additionally, WL-1 formula treatment accelerated daily weight loss by 250%. This finding suggests that, if the same occurred in humans, WL-1 as part of a dietary weight loss regimen might help young obese patients lose weight more quickly. In the US, the prevalence of obesity in individuals over 40 is much higher than that in younger individuals (2) and lifestyle changes including dietary modification have been difficult as a means to stable weight loss for the majority of middle-aged to senior adults. In a second experiment, we employed older mice ("middle-aged") compared to those in experiment 1 to evaluate if WL-1 would also suppress HFD induced weight gain without dietary intervention. We found that WL-1 suppressed daily body weight gain in these mice by approximately 800% as compared to sham treatment. Consistently, WL-1 also reduced epididymal fat weight. If W1-1 were to have the same effects in humans, WL-1 might help limit weight gain in the absence of appetite suppression medications and reduced calorie intake interventions. An additional significant beneficial effect of WL-1 treatment on HFD fed middle-aged mice was reduction of blood cholesterol and glucose levels. If the same results occur in humans, WL-1 may be valuable in treating pre-metabolic syndrome and perhaps metabolic syndrome.

Since WL-1 reduced body weight gain and normalized cholesterol and glucose levels without suppression of appetite in HFD fed mid age mice, we hypothesized that WL-1 may affect signaling pathways involved in glucose and cholesterol metabolism. Previous research showed that activation of PPARγ is mainly involved in regulating lipid metabolism, insulin sensitivity, and glucose homeostasis and its agonist has been used in the treatment of hyperlipidemia and type 2 diabetes. (20) PPARγ reduces cholesterol synthesis and is also important in energy metabolism. (21;22) In animal study, activation of PPARγ increased insulin sensitivity and reduced the glucose levels in circulation and liver through the regulation of the adipocyte-specific secretory protein, Acrp30(23). We found that PPARγ gene expression was significantly increased in epididymal fat tissue from WL-1 treated mice compared to the sham treated mice. This might, at least in part, explain the decreased glucose and cholesterol serum levels in this study. Fatty-acid-binding protein (FABP-4) is predominantly expressed in adipose tissue. Recent research found that adipose tissue in obese individuals exhibited lower FABP4 gene expression than adipose tissue from lean individuals (24;25) We found that adipose tissue FABP4 gene expression was significantly increased by WL-1 treatment. This increased FABP4 expression might have led to the decreased glucose levels and body weight. We also measured gene expression of CPT1, UCP2, which are related to mitochondrial fatty acid oxidation (26;27), and AMPK, which is important in energy metabolism. (28) All showed a trend of increased expression levels in WL-1 treated group. Since WL-1 did not affect food intake, but did significantly reduce body weight, accompanied by significant reduction of blood cholesterol and glucose levels, we hypothesize that WL-1 treatment might induce body weight loss through regulating the expression of energy metabolism genes. In addition to increasing insulin sensitivity and reducing glucose levels, PPAR γ also has a minor adipogenesis effect. (20) In our model, PPAR γ may have acted with FABP4, and perhaps CPT1, UCP2 and AMPK to increase metabolism and suppress weight gain. At present, it is unknown which active compounds in WL-1 modulate these gene expressions or molecular mechanisms underlying this gene regulation, so further investigation is required.

The safety of all herbs in WL-1 is well documented (10;29). Notably, this formula does not contain the stimulant Ma Huang (Ephedra sinica), which has significant safety concerns when used for weight loss at large doses. (7) We also conducted standard acute and sub-chronic toxicity studies in mice. No mortality or morbidity was observed and no abnormal changes, such alterations in food and water intake, or diarrhea, were observed. Biochemical analysis data and hematological data also showed that WL-1 has a large safety margin. In conclusion, we present for the first time evidence of the safety and effectiveness of the Chinese herbal medicine formula, WL-1, in high-fat-diet induced obesity in a murine model.

WL-1 treatment augmented young obese mice weight loss after switching to a reduced calorie diet. It also prevented weight gain in older mice without changing their high fat diet. In addition, beneficial effects were observed on serum cholesterol and glucose levels, perhaps due to modulation of expression of energy metabolism genes such as PPAR γ and FABP4.

Example 2

Methods:
A. Preparation of the Formulations
W-LHIT:
W-LHIT formulation was developed with dried aqueous extracts of 6 Chinese herbal medicines-*Ganoderma lucidum*, rhizome of *Coptis chinensis, Radix astragali, Nelumbo nucifera* Gaertn, *Chaenomeles speciosa*, and *Fructus aurantii*. All raw herbs are Chinese origin. All herbs were extracted with water and then concentrated and dried according to the standard decocting and drying manufacturing process. The dried powder extract was packaged and stored at room temperature in a dry and well-ventilated botanical storage.

High pressure liquid chromatography (HPLC) fingerprinting was used as a means of standardization of botanical products. The HPLC fingerprint of W-LHIT was generated using a Waters 2690 HPLC coupled with photodiode array detector (PDA; Waters, Milford, Mass.). 100 mg of W-LHIT was dissolved into 1 mL of CH3CN and 0.1% formic acid mixture (1:1 ratio). The solution was filtered through Whatman 0.45 µm syringe filters (Whatman Inc., Clifton, N.J.). 10 µL of filtered solution was injected and analyzed on a ZORBAX SB-C18 (4.6×150 mm, 5 µm) column (Agilent, Santa Clara, Calif.). 0.1% aqueous formic acid was used as mobile phase A and CH3CN was used as mobile phase B with a constant flow rate of 1.0 mL/min. The gradient was started at 2% B and linearly went up to 25% B within 45 min, then to 35% B within 25 min, to 55% B within 15 min, to 75% B within 10 min, and maintained at 75% B for 5 min. Waters' Empower software was used for data collection and analysis. A total of 21 major peaks were present in the HPLC fingerprint (FIG. 1). Twelve compounds were characterized by Liquid chromatography-mass spectrometry (LC-MS) as quercetin 3-O-glucuronide from *Nelumbo nucifera* Gaertn; hesperidin, nobiletin, tangeretin, and 3-hydroxy-5,6,7,8,3', 4'-hexamethoxyflavone from *Fructus aurantii*; jatrorrhizine, coptisine, and berberine from rhizome of *Coptis chinensis*; astragaloside IV from *Radix astragali*; ganolucidic acid D, ganoderic acid K, and ganoderic acid H from *Ganoderma lucidum*. Three batches of W-LHIT products were generated. HPLC fingerprints of each individual herbal medicine and comparison of peak intensities of identified compounds were used to monitor the quality of different batches of W-LHIT product. Berberine was used as the key index compound.

W-LHIT-B:
Butanol extracts of W-LHIT (W-LHIT-B) were prepared in the laboratory. 10 g of W-LHIT formula was ground into fine powder and dissolved into 200 mL of DDH2O. Equal volume of Butanol was fully mixed with the W-LHIT solution and the mixture was transferred into a separatory funnel. Separated butanol extracts were collected. The butanol extract was then mixed with distilled water (3:1 ratio)

and evaporated under reduced pressure using a Rotary evaporator. The dried extract (W-LHIT-B) was stored at room temperature.

W-LHIT-C:

W-LHIT-C was formed from the same constituent herbs as W-LHIT with the *Chaenomeles speciosa* not present, serially extracted with water followed by butanol. This formula was generated by combination of butanol extracts of rhizome of *Coptis chinensis* (about 30-90%), *Radix astragali* (about 0.5-20%) *Fructus Aurantii* (about 0.5-20%), *Ganoderma lucidum* (about 0.5-40%), and *Nelumbo nucifera* Gaertn (about 0.5-20%). Each individual herbal component was extracted using butanol from the dried aqueous extract and dried under vacuum. The yield was 25%, 11.6%, 31.6%, 12%, and 32.5% respectively.

B. Administration:

Each mouse received 84 mg of W-LHIT, or 100 mg of W-LHIT-B, or 8.4 mg of W-LHIT-C daily. All medicines were dissolved in 1.0 mL of drinking water, and intragastrically (i.g.) administered by two separated feedings (0.5 mL per feeding 4 hours apart using a standard mouse feeding needle (VWR, Radnor, Pa.). The Sham group was fed with equal volume of drinking water as the control.

Body weight and food consumption amounts were recorded three times a week. Body weight gain was calculated by subtracting body weight on the first day from that on the last day of treatment. Daily body weight gain was calculated by dividing body weight gain by the number of treatment days. Chow was weighed three times a week during the period of acclimatization and treatment, and daily food consumption was calculated by dividing total food consumption by the number of days.

C. Results:

The butanol extract of W-LHIT was collected, dried, weighed, and named as W-LHIT-B. The W-LHIT-B extract mostly contains the relatively less-polar components, such as alkaloid, flavonoid, and saponin. The yield of W-LHIT-B was calculated as 23%.

Figures 9A, 9B, 9C:
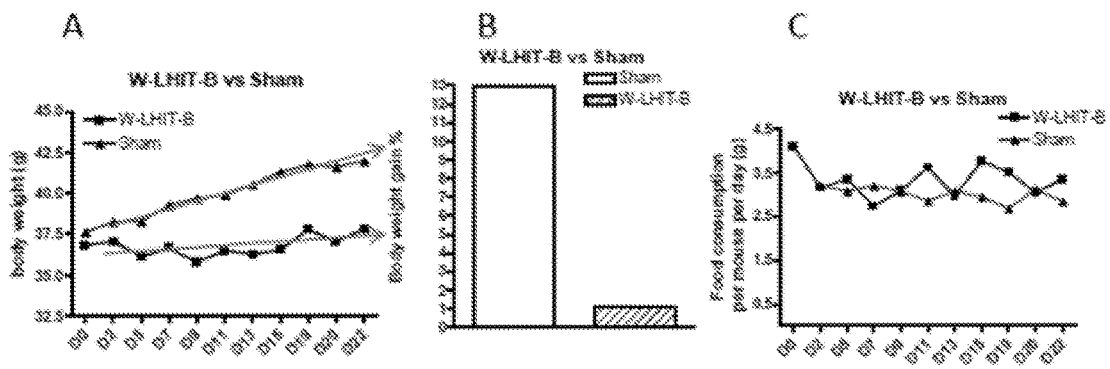
FIGS. 9A-9C. The effects of W-LHIT-B on body weight and food intake. (A) Body weight (g) of W-LHIT-B versus Sham treated mice over time (B) Body weight gain percentage of W-LHIT-B versus Sham treated mice (C) Food consumption per mouse per day(g) of W-LHIT-B versus Sham treated mice over time.

Consistently, W-LHIT formula suppressed body weight gain in HFD fed older obese mice as shown in the previously completed experiment. After thirty days of treatment, sham treated mice body weight increased by 13% while on HFD (FIG. 9A,9B). In contrast, W-LHIT treated obese mice (HFD/W-LHIT) increased body weight by only 4.5% (FIG. 9A,9B).

Figures 10A, 10B, 10C:
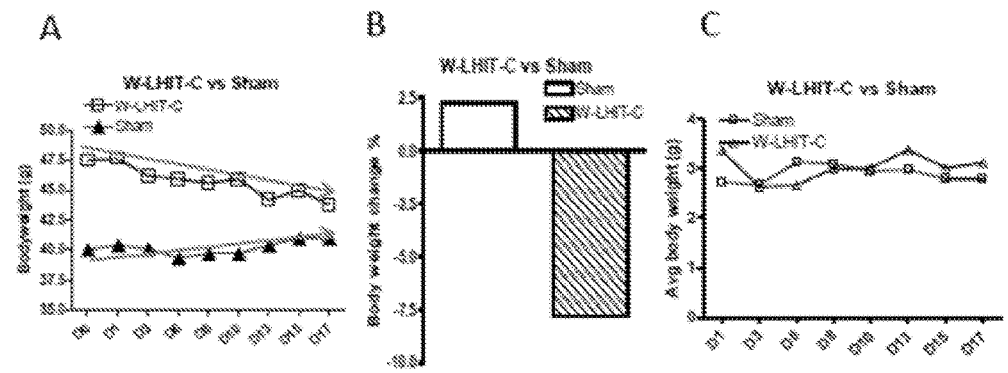
FIGS. 10A-10C. The effects of W-LHIT-C on body weight and food intake. (A) Body weight (g) of W-LHIT-C versus Sham treated mice over time (B) Body weight change percentage of W-LHIT-C versus Sham treated mice (C) Average body weight(g) of W-LHIT-C versus Sham treated mice over time.

In W-LHIT-B treated group, the body weight of obese mice only increased 1% (FIG. 10A, 10B). Food intake did not differ between W-LHIT treated and sham-treated mice while on HFD (FIG. 9C). There was fluctuation of food consumption in the W-LHIT-B treated group; however, no significant difference from the Sham treated group was observed (FIG. 10C). W-LHIT-B showed stronger suppression of weight gain at nearly similar doses for the same treatment duration.

The W-LHIT-C showed decreased body weight (FIG. 11A) compared with the sham group. In this experiment, the starting body weight of the tested group of mice was extremely high, which is about 158% of the body weight of the normal mice (~30 g). Even at this condition, the W-LHIT-C still had effect.

REFERENCES

1. World Health Organization. Obesity and overweight. http://www.whoint/mediacentre/factsheets/fs311/en/ (updated 2013) 2008. 391
2. Flegal K M, Carroll M D, Ogden C L, Curtin L R. Prevalence and trends in obesity among US adults, 1999-2008. JAMA 2010; %20; 303:235-41.
3. Kopelman P G. Obesity as a medical problem. Nature 2000; 404:635-43.
4. Bardou M, Barkun A N, Martel M. Obesity and colorectal cancer. Gut 2013; 62:933-47.
5. Maynard L M, Serdula M K, Galuska D A, Gillespie C, Mokdad A H. Secular trends in desired weight of adults. Int J Obes (Lond) 2006; 30:1375-81. 397
6. Maahs D, de Serna D G, Kolotkin R L, Ralston S, Sandate J, Qualls C, Schade D S. Randomized, double-blind, placebo-controlled trial of orlistat for weight loss in adolescents. Endocr Pract 2006; 12:18-28.
7. Manore M M. Dietary supplements for improving body composition and reducing body weight: where is the evidence? Int J Sport Nutr Exerc Metab 2012; 22:139-54.
8. U.S. Food and Drug Administration (FDA). FDA warns consumers about Brazilian diet pills found to contain active drug ingredients. http://www.fdagov/newsevents/newsroom/pressannouncements/2006/ucm108578 htm 2006.
9. Wong W L. Obesity. In: Chen G T, Yang S S, eds. Practical Diagnostics and Therapeutics of Integrated Traditional Chinese and Western Medicine. Beijing: China Medicine Pharmacology Science and Technology Publisher, 1993: 683-9.
10. The State Pharmacopoeia Commission of The People's Republic of China. Pharmacopoeia of the People's Republic of China, Version 6 ed. People's Medical Publishing House, 2005:1-791 pp.
11. Hariri N, Thibault L. High-fat diet-induced obesity in animal models. Nutr Res Rev 2010; 23:270-99.
12. Institute of Laboratory Animal Resources Commission of Life Sciences NRC. Guide for the Care and Use of Laboratory Animals. National Academy Press, 1996.
13. Blue Light, Inc. http://www treasureofeast com/index php?main_page=about 2013.
14. Dolan S P, Nortrup D A, Bolger P M, Capar S G. Analysis of dietary supplements for arsenic, cadmium, mercury, and lead using inductively coupled plasma mass spectrometry. J Agric Food Chem 2003; 51:1307-12.
15. Caldas E D, Machado L L. Cadmium, mercury and lead in medicinal herbs in Brazil. Food Chem Toxicol 2004; 42:599-603.
16. Raman P, Patino L C, Nair M G. Evaluation of metal and microbial contamination in botanical supplements. J Agric Food Chem 2004; 52:7822-7.
17. The state of administration of Traditional Chinese Medicine of the People's Republic of China. Standards of Import and Export of Green Medicinal Plants and Their Preparations. Ministry of Foreign Trade and Economic Cooperation, People's Republic of China 2001.
18. Xiu S Y. The Experimental Method of Pharmacology. Beijing: The People's Public Health Publisher, 1986:985-924 pp. 428 19. Alexander J, Chang G Q, Dourmashkin J T, Leibowitz S F. Distinct phenotypes of obesity-prone AKR/J, DBA2J and C57BL/6J mice compared to control strains. Int J Obes (Lond) 2006; 30:50-9.
20. Monsalve F A, Pyarasani R D, Delgado-Lopez F, Moore-Carrasco R. Peroxisome proliferator-activated receptor targets for the treatment of metabolic diseases. Mediators Inflamm 2013; 2013:549627.
21. Klopotek A, Hirche F, Eder K. PPAR gamma ligand troglitazone lowers cholesterol synthesis in HepG2 and Caco-2 cells via a reduced concentration of nuclear SREBP-2. Exp Biol Med (Maywood)) 2006; 231:1365-72.
22. Li T, Chiang J Y. Regulation of bile acid and cholesterol metabolism by PPARs. PPAR Res 2009; 2009:501739.
23. Berg A H, Combs T P, Scherer P E. ACRP30/adiponectin: an adipokine regulating glucose and lipid metabolism. Trends Endocrinol Metab 2002; 13:84-9.
24. Clemente-Postigo M, Queipo-Ortuno M I, Fernandez-Garcia D, Gomez-Huelgas R, Tinahones F J, Cardona F. Adipose tissue gene expression of factors related to lipid processing in obesity. PLoS One 2011; 6:e24783.
25. Queipo-Ortuno M I, Escote X, Ceperuelo-Mallafre V, Garrido-Sanchez L, Miranda M, Clemente-Postigo M et al. FABP4 dynamics in obesity: discrepancies in adipose tissue and liver expression regarding circulating plasma levels. PLoS One 2012; 7:e48605.
26. Boss O, Hagen T, Lowell B B. Uncoupling proteins 2 and 3: potential regulators of mitochondrial energy metabolism. Diabetes 2000; 49:143-56.
27. Jambor de Sousa U L, Koss M D, Fillies M, Gahl A, Scheeder M R, Cardoso M C et al. CPT1 alpha overexpression increases long-chain fatty acid oxidation and reduces cell viability with incremental palmitic acid concentration in 293T cells. Biochem Biophys Res Commun 2005; 338:757-61.
28. Canto C, Auwerx J. AMP-activated protein kinase and its downstream transcriptional pathways. Cell Mol Life Sci 2010; 67:3407-23.
29. Bensky D C S, Stoger E. Chinese Herbal Medicine: Material and Meidica., 3rd ed. Seattle: Eastland Press, Inc., 2004:1-1311 pp.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

What is claimed is:

1. A method for decreasing body weight in a subject in need thereof comprising the steps of administering a pharmacologically effective dose of a formulation comprising extracts of *Ganoderma lucidum*, rhizome of *Coptis chinensis, Radix astragali, Nelumbo nucifera Gaertn*, and *Fructus Aurantii*.

2. The method of claim 1 wherein the extracts are aqueous extracts.

3. The method of claim 1 wherein the extracts have been serially extracted with water followed by butanol.

4. The method of claim 1 wherein the subject is on a high calorie diet.

5. The method of claim 1 wherein the subject in on a reduced calorie diet.

6. The method of claim 1 wherein the decrease in body weight is affected through the reduction of epididymal adipose tissue.

7. The method of claim 1 wherein the decrease in body weight is affected through the reduction in visceral fat.

8. The method of claim 1 wherein the subject is a mammal.

9. The method of claim 1 wherein the subject is human.

10. A method for affecting biological sequelae of obesity in a subject in need thereof comprising the steps of administering to the subject a pharmacologically effective dose of a formulation comprising extracts of *Ganoderma lucidum*, rhizome of *Coptis chinensis, Radix astragali, Nelumbo nucifera Gaertn*, and *Fructus Aurantii*.

11. The method of claim 10 wherein the biological sequelae of obesity being affected is the reduction of serum cholesterol.

12. The method of claim 10 wherein the biological sequelae of obesity being affected is the reduction of glucose levels.

13. The method of claim 10 wherein the extracts are aqueous extracts.

14. The method of claim 10 wherein the extracts have been serially extracted with water followed by butanol.

15. The method of claim 10 wherein the subject is human.

16. A method for affecting gene expression associated with obesity in a subject in need thereof comprising the steps of administering to the subject a pharmacologically effective dose of a formulation comprising extracts of *Ganoderma lucidum*, rhizome of *Coptis chinensis, Radix astragali, Nelumbo nucifera Gaertn*, and *Fructus Aurantii*.

17. The method of claim 16 wherein the gene altered is selected from the group consisting of PPARγ, FABP4, CPT1, UCP2, and AMPK.

18. The method of claim 16 wherein the extracts are aqueous extracts.

19. The method of claim 16 wherein the extracts have been serially extracted with water followed by butanol.

20. The method of claim 16 wherein the gene expression is increased.

21. The method of claim 16 wherein the subject is human.

22. A method for decreasing body weight in a subject in need thereof comprising the steps of administering a pharmacologically effective dose of a formulation comprising extracts of *Ganoderma lucidum*, rhizome of *Coptis chinensis, Radix astragali, Nelumbo nucifera Gaertn, Fructus Aurantii*, and *Chaenomeles speciosa*.

23. The method of claim 22 wherein the extracts are aqueous extracts.

24. The method of claim 22 wherein the extracts have been serially extracted with water followed by butanol.

25. The method of claim 22 wherein the subject is on a high calorie diet.

26. The method of claim 22 wherein the subject in on a reduced calorie diet.

27. The method of claim 22 wherein the decrease in body weight is affected through the reduction of epididymal adipose tissue.

28. The method of claim 22 wherein the decrease in body weight is affected through the reduction in visceral fat.

29. The method of claim 22 wherein the subject is a mammal.

30. The method of claim 22 wherein the subject is human.

31. A method for affecting biological sequelae of obesity in a subject in need thereof comprising the steps of administering to the subject a pharmacologically effective dose of a formulation comprising extracts of *Ganoderma lucidum*, rhizome of *Coptis chinensis, Radix astragali, Nelumbo nucifera Gaertn, Fructus Aurantii*, and *Chaenomeles speciosa*.

32. The method of claim 31 wherein the biological sequelae of obesity being affected is the reduction of serum cholesterol.

33. The method of claim 31 wherein the biological sequelae of obesity being affected is the reduction of glucose levels.

34. The method of claim 31 wherein the extracts are aqueous extracts.

35. The method of claim 31 wherein the extracts have been serially extracted with water followed by butanol.

36. The method of claim 31 wherein the subject is human.

37. A method for affecting gene expression associated with obesity in a subject in need thereof comprising the steps of administering to the subject a pharmacologically effective dose of a formulation comprising extracts of *Ganoderma lucidum*, rhizome of *Coptis chinensis, Radix astragali, Nelumbo nucifera Gaertn, Fructus Aurantii*, and *Chaenomeles speciosa*.

38. The method of claim 37 wherein the gene altered is selected from the group consisting of PPARγ, FABP4, CPT1, UCP2, and AMPK.

39. The method of claim 37 wherein the extracts are aqueous extracts.

40. The method of claim 37 wherein the extracts have been serially extracted with water followed by butanol.

41. The method of claim 37 wherein the gene expression is increased.

42. The method of claim 37 wherein the subject is human.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide

<400> SEQUENCE: 1
tttcaagggt gccagttt                                                 18

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2
gaggccagca tcgtgtag                                                 18

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide

<400> SEQUENCE: 3
aaatcaccgc agacgaca                                                 18

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide

<400> SEQUENCE: 4
cacattccac caccagct                                                 18

<210> SEQ ID NO 5

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
agtatggagc agacgcaatc                                              20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
ctctccgacc acgtattctt                                              20
```